United States Patent
Cavallaro (10) Patent No.: US 9,463,210 B1
(45) Date of Patent: Oct. 11, 2016

(54) METHOD FOR ALLEVIATING CRAVINGS AND DISCOMFORT ASSOCIATED WITH SMOKING CESSATION8

(71) Applicant: Antonino Cavallaro, Miami, FL (US)

(72) Inventor: Antonino Cavallaro, Miami, FL (US)

( * ) Notice: Subject to any disclaimer, the term of this patent is extended or adjusted under 35 U.S.C. 154(b) by 0 days.

(21) Appl. No.: 14/877,664

(22) Filed: Oct. 7, 2015

(51) Int. Cl.
| | |
|---|---|
| *A01N 65/00* | (2009.01) |
| *A61K 36/53* | (2006.01) |
| *A61K 36/258* | (2006.01) |
| *A61K 31/455* | (2006.01) |
| *A61K 31/197* | (2006.01) |
| *A61K 31/685* | (2006.01) |
| *A61K 31/352* | (2006.01) |

(52) U.S. Cl.
CPC .............. *A61K 36/53* (2013.01); *A61K 31/197* (2013.01); *A61K 31/352* (2013.01); *A61K 31/455* (2013.01); *A61K 31/685* (2013.01); *A61K 36/258* (2013.01)

(58) Field of Classification Search
CPC ........................................................ A61K 36/00
USPC ............................................................ 424/725
See application file for complete search history.

(56) References Cited

U.S. PATENT DOCUMENTS 7,906,325 B2 * 3/2011 Bryan .................. C12N 9/1029 435/320.1

\* cited by examiner

*Primary Examiner* — Michael Meller
(74) *Attorney, Agent, or Firm* — Mark Terry (57) ABSTRACT

A method for alleviating cravings and discomfort of a user due to nicotine addiction upon immediate cessation of tobacco by said user, comprising the steps of inhaling, upon commencement of a nicotine craving episode, for about 10 minutes, between about 3 to 5 drops of rosemary essential oil, wherein said rosemary essential oil is sprinkled on an apposite vaporizer pad, orally ingesting between about 250 mg to 500 mg of niacinamide, orally ingesting between about 200 mg to 300 mg of sarcosine, orally ingesting between about 300 mg to 600 mg of red Korean *ginseng* extract, and orally ingesting about 500 mg of soy lecithin.

1 Claim, 8 Drawing Sheets

Niacinamide

Procedure    In healthy human volunteers took nicotinamide doses up to 6 g in gelatine capsules. Plasma peak levels were measured from serial blood samples taken within 24 h. after administration of nicotinamide. Samples were analysed by HPLC/UV.
Mice were injected i.p. with 100-1000 mg/kg nicotinamide in 0.9% NaCl and a single blood sample was collected several times during 6 h after dosing.

Results    Plasma peak levels for nicotinamide were attained in the human volunteers within 45 min. after ingestion. Peak plasma levels were dose dependent with a maximum of 160 µg/ml. Elimination half-life was also dose dependent, although not linear.
Mice injected with nicotinamide showed similar characteristics as the human data, although elimination half-lives were not dose dependent.
Side effects such headache, dizziness and nausea were mild and transient at 6 g.

|  | Dose (g) | Peak conc. (µg/ml) | T1/2 (h) | AUC (mg/ml x min.) |
|---|---|---|---|---|
| Human | 1 | 21-36 | 1.1-3.8 | 3.2-6.3 |
|  | 3 | 56-107 | 4.3-8.8 | 21.1-39.5 |
|  | 6 | 120-190 | 6-11.5 | 78.7-132 |
| Mouse | 0.1 | 100 | 2.1 | 209 |

Ginsenosides

Forskolin

| Molecule | Dosage | Frequency |
|---|---|---|
| Rosemary Essential Oil | 3 to 5 drops of commercial Rosemary essential oil will be sprinkled on the apposite vaporizer pad, and subject will inhale (nicotine craving episode) for 10 minutes | On demand with a maximum frequency of 5 times/day |
| Niacinamide | 250 mg to 500 mg oral, depending on subject weight | Every 12 hours |
| Sarcosine | 200mg to 300 mg oral, depending on subject weight | Every 3 hours, maximum of 5 times/day |
| Red Korean Ginseng extract (standarized 15% ginsenosides) | 300mg to 600 mg oral | Every 12 hours |
| Optional: Forskolin (standarized abstract 10%) | 125 to 250 mg oral | Every 12 hours |
| Soy Lecithin | 500 mg oral | Once a day |

METHOD FOR ALLEVIATING CRAVINGS AND DISCOMFORT ASSOCIATED WITH SMOKING CESSATIONS

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The present invention relates to generally to smoking cessation, and more specifically, to the methods and treatments for alleviating cravings and discomfort upon cessation of tobacco use sustained by nicotine addiction.

BACKGROUND

Tobacco is a product prepared by curing the leaves of the tobacco plant. The plant is categorized within the genus *Nicotiana* of the Solanaceae (nightshade) family. There are over 70 species of tobacco. Once of the main commercial tobacco crops is *N. tabacum*. Another species, *N. rustica*, is also widely used around the world. Tobacco contains the alkaloid nicotine, a stimulant. Dried tobacco leaves are mainly smoked in cigarettes, cigars, pipe tobacco, and flavored shisha tobacco. They are also consumed as snuff, chewing tobacco, and dipping tobacco.

Tobacco addiction is a major health problem in the United States, accounting for more preventable illnesses and deaths than any other single factor. According to the Centers for Disease Control and Prevention (CDC), cigarette smoking causes more than 480,000 deaths each year in the Unites States alone, or about one in five deaths. Tobacco use is a major cause of death from cancer, cardiovascular disease, and pulmonary disease. Tobacco addiction is also a major health problem worldwide.

Smoking-caused disease is a consequence of exposure to toxins in tobacco smoke and nicotine delivered though tobacco products sustains addictive tobacco use, which in turn causes much premature disability and death. In many cases, those who attempt to quit smoking have cravings and discomfort upon the cessation of tobacco, which are sustained by the nicotine addiction. These cravings and discomfort are some of the reasons why, despite knowing the health risks associated with smoking, many users continue to smoke cigarettes as well as use other products containing nicotine.

About 40 percent of smokers in the United States try to quit every year. Success rates are meager as only 3 to 6 percent of those attempting to quit succeed in avoiding smoking for 6 to 12 months, while the majority of quit attempts fail within the first 8 days. As of mid-2015, the Food and Drug Administration (FDA) has approved nicotine replacement therapy (NRT), and a few other drugs, as smoking-cessation medications, all with success rates at the end of one year falling short of 25%.

Therefore, a need exists to overcome the problems with the prior art as discussed above, and particularly for a more efficient way of alleviating cravings and discomfort associated with cessation of tobacco use sustained by nicotine addiction.

SUMMARY

This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The claimed subject matter is directed to methods or treatment protocols for alleviating cravings and discomfort of a user due to nicotine addiction upon immediate cessation of tobacco by said user, comprising the steps of: inhaling, upon commencement of a nicotine craving episode, for about 10 minutes, about between 3 to 5 drops of rosemary essential oil, wherein said rosemary essential oil is sprinkled on an apposite vaporizer pad; orally ingesting an amount of niacinamide, wherein said amount of niacinamide is about between 250 mg to 500 mg; orally ingesting an amount of sarcosine, wherein said amount of sarcosine is about between 200 mg to 300 mg; orally ingesting an amount of red Korean *ginseng* extract, wherein said amount of red Korean *ginseng* extract is about between 300 mg to 600 mg; and, orally ingesting, an amount of soy lecithin, wherein said amount of soy lecithin is about 500 mg.

To the accomplishment of the above and related objects, the claimed subject matter may be embodied in the form illustrated in the accompanying drawings, attention being called to the fact, however, that the drawings are illustrative only, and that changes may be made in the specific construction illustrated and described within the scope of the appended claims. The foregoing and other features and advantages of the claimed subject matter will be apparent from the following more particular description of the preferred embodiments of the invention, as illustrated in the accompanying drawings.

BRIEF DESCRIPTION OF THE DRAWINGS

The accompanying drawings, which are incorporated in and constitute part of this specification, illustrate embodiments of the claimed subject matter and together with the description, serve to explain the principles of the disclosed embodiments. The embodiments illustrated herein are presently preferred, it being understood, however, that the claimed subject matter is not limited to the precise arrangements and instrumentalities shown, wherein:

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments provide methods or treatment protocols for alleviating cravings and discomfort of a user due to nicotine addiction upon immediate cessation of tobacco by said user. The claimed subject matter improves over the prior art by providing a safer and innocuous anti-inflammatory molecules capable of crossing the blood brain barrier in order to alleviate cravings and discomfort of a user due to nicotine addiction upon immediate cessation of tobacco. The disclosed treatment protocol reduces or alleviates cravings and discomfort sustained by nicotine addiction, which may increase the success rate for a person to discontinue smoking, and as a result may reduce the risk factors associated with continuing to use tobacco products.

During withdrawal from nicotine, as the G-protein coupling to the gamma-Aminobutyric acid (GABA) molecule is faulty and hence significantly reduced in the pre fontal cortex, the dopaminergic neurotransmission controls in the brain reward center is sloppy and reduced at best, generating the anxiety, lack of patience and crankiness commonly observed in studied individuals during the withdrawal experience. If acetylcholine levels are in fact downregulated, then proper plasma glucose balance will be impaired. A study from Wada T. et al. confirms that a higher level of risk of metabolic syndrome persists 20 years after the cessation of smoking, when compared to never smokers. The metabolic syndrome abnormalities include, among others, glucose intolerance. Given the demonstrated ability of nicotine to upregulate il-1 and in turn because of the latter action, upregulation of iNOS expression of nitric oxide in astrocytes and microglia, and taking into consideration that serine racemase enzyme function is known to be regulated/inhibited by nitric oxide (NO), then it is plausible to suspect that pathological high levels of NO can impair glutamatergic NMDAR neurotransmission since D-serine levels might be presumably too low. Hence, a goal is to administer safe and innocuous anti-inflammatory molecules, capable of crossing the blood brain bather (BBB).

Figure 1:
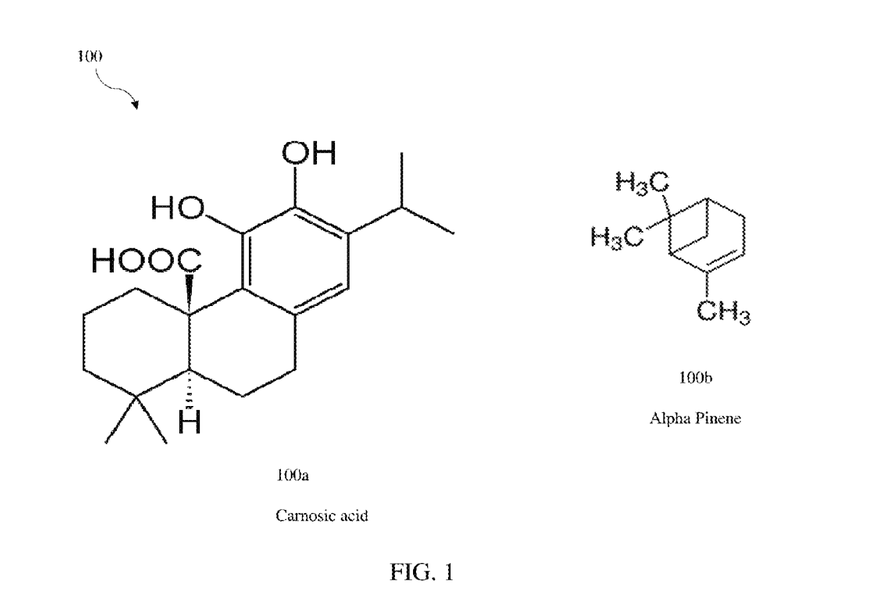
FIG. 1 is a perspective view of the molecular structures of carnosic acid and Alpha-Pinene components of rosemary essential oil, according to an example embodiment.
Figure 2:
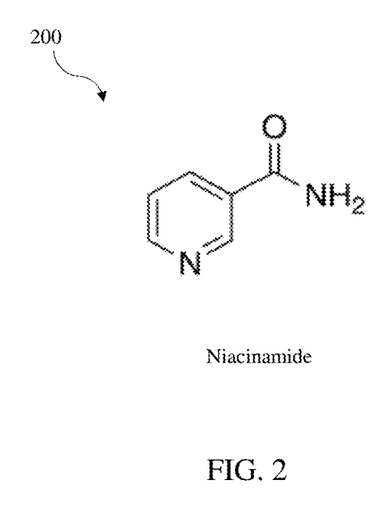
FIG. 2 is a perspective view of the molecular structure of niacinamide, according to an example embodiment.

Referring to FIG. 1, carnosic acid 100a is a diterpene molecule found in rosemary (*Rosmarinus Officinalis*) and sage (*Salvia officinalis*) evergreen shrubs. Diterpene is a type of terpene, an organic compound composed of four isoprene units and has the molecular formula C20H32. They derive from geranylgeranyl pyrophosphate. Diterpenes form the basis for biologically important compounds such as retinol, retinal, and phytol. They are known to be antimicrobial and anti-inflammatory. Its molecular formula is C20H28O4, with a molecular weight of 332.43392 g/mol. FIG. 1 is a perspective view of the 2D structure of carnosic acid. Quoting Petiwala et al., "recently, rosemary extracts standardized to diterpenes (e.g. carnosic acid and carnosol) have been approved by the European Union (EU) and given a GRAS (Generally Recognized as Safe) status in the United States by the Food and Drug Administration (FDA). Incorporation of rosemary into our food system and through dietary selection (e.g. Mediterranean Diet) has increased the likelihood of exposure to diterpenes in rosemary." The acute oral toxicity study in Kuming mice design followed the OECD-guidelines 423, and a 30-day chronic oral toxicity study in Wistar rats based on the enhanced OECD test guideline 407 were performed. The result found was that the oral lethal dose (LD50) for mice was 7100 mg/kg of body weight in the acute toxicity study.

According to a recent study and other conclusions of the inventor: "Inflammatory mediators and cytokines play important roles in the pathogenesis of a vast number of human diseases; therefore much attention is focused on blunting their proinflammatory modes of action. The aims of the present research were to assess the effectiveness of combinations of carotenoids and phenolics, at concentrations that can be achieved in blood, to inhibit the release of inflammatory mediators from macrophages exposed to lipopolysaccharide (LPS) and to determine what the anti-inflammatory effect of the phytonutrient combinations was in an in vivo mouse model of peritonitis. Preincubation of mouse peritoneal macrophages with lycopene (1 µM) or Lyc-O-Mato (1 µM) and carnosic acid (2 µM), lutein (1 µM), and/or β-carotene (2 µM) 1 h before addition of LPS for 24 h caused a synergistic inhibition of NO, prostaglandin E2, and superoxide production derived from downregulation of iNOS, COX-2, and NADPH oxidase protein and mRNA expression and synergistic inhibition of TNFα secretion. The anti-inflammatory action of the phytonutrient combinations used probably resides in their antioxidant properties, because they caused an immediate, efficient, and synergistic inhibition of LPS-induced internal superoxide production leading to a marked decrease in ERK and NF-κB activation. The anti-inflammatory effects of the selected phytonutrient combinations were also demonstrated in a mouse model of peritonitis: their supplementation in drinking water resulted in attenuation of neutrophil recruitment to the peritoneal cavity and in inhibition of inflammatory mediator production by peritoneal neutrophils and macrophages."

It has been proven that carnosic acid can downregulate iNOS in the wake of its broad anti-inflammatory action in vivo in mouse. It also has been proven for human brain anti-inflammatory purposes. Quoting Mika Yanagitai et al. "In the previous studies, we reported that carnosic acid (CA) protects cortical neurons by activating the Keap1/Nrf2 pathway, which activation is initiated by S-alkylation of the critical cysteine thiol of the Keap1 protein by the 'electrophilic' quinone-type CA. Here, we found that the pro-electrophilic CA inhibited the in vitro lipopolysaccharide (LPS)-induced activation of cells of the mouse microglial cell line MG6. LPS induced the expression of IL-1β and IL-6, typical inflammatory cytokines released from microglial cells. CA inhibited the NO production associated with a decrease in the level of inducible NO synthase. Neither CA nor LPS affected cell survival at the concentrations used here. These actions of CA seemed to be mediated by induction of phase 2 genes (gclc, gclm, nqo1 and xct). We propose that an inducer of phase 2 genes may be a critical regulator of microglial activation. Thus, CA is a unique pro-electrophilic compound that provides both a protective effect on neurons and an anti-inflammatory one on microglia through induction of phase 2 genes."

Finally, to confirm that carnosic acid is able to cross the blood brain barrier (BBB), let us quote Tayebeh Rezaie et al's work: "The herb rosemary has been reported to have antioxidant and anti-inflammatory activity. We have previously shown that carnosic acid (CA), present in rosemary extract, crosses the blood-brain barrier to exert neuroprotective effects by upregulating endogenous antioxidant enzymes via the Nrf2 transcriptional pathway."

According to Simon Mills and Kerry Bone's book "The Essential Guide to Herbal Safety", "rosemary contains an essential oil (1% to 2%), the composition of which varies (three main chemotypes are found growing in Europe). The major constituents of rosemary essential oil are 1,8-cineole, alpha-pinene, and camphor. Other constituents include phenolic diterpenes (such as carnosol and carnosic acid), rosmarinic acid, flavonoids and triterpenoids". As if this was not enough, the prevalent compounds by concentration in rosemary essential oil are alpha-pinene and camphene.

Referring to 100b, alpha-pinene 100b is an organic compound of the terpene class, one of two isomers of pinene. It is an alkene and it contains a reactive four-membered ring. It is found in the oils of many species of many coniferous trees, notably the pine. It is also found in the essential oil of rosemary (*Rosmarinus officinalis*).

From its Material Safety Data Sheet: Rat oral LD50 values are available for alpha-pinene, beta-pinene, camphene and turpentine oil and indicate these materials to be very low in oral acute toxicity with LD50 values in the range from 3388 mg/kg to greater than 5000 mg/kg. Rabbit dermal LD50 values similarly indicate very low toxicities with values greater than the limit doses of 2000 or 5000 mg/kg.

Quoting the work of Neves et al.: "Nuclear factor-κB is a key transcription factor activated by pro-inflammatory signals, like interleukin-1β (IL-1), being required for the expression of many inflammatory and catabolic mediators, such as nitric oxide (NO), that play an important role in arthritic diseases. This work aimed at screening and identifying natural inhibitors of IL-induced NF-κB activation and NO production in human articular chondrocytes. Five essential oils obtained from four plants of the Iberian flora, *Mentha×piperita* L. (Lamiaceae), *Origanum virens* L. (Lamiaceae), *Lavandula luiseri* L. (Lamiaceae), and *Juniperus oxycedrus* L. subsp. *oxycedrus* (Cupressaceae), were screened for their ability to prevent IL-1-induced NO production. The oil showing higher inhibitory activity was fractionated, concentrated, analyzed for composition elucidation and prepared for further assays. For this purpose, the human chondrocytic cell line C-28/I2 was used to evaluate NF-κB activation by determining the cytoplasmic levels of the total and phosphorylated forms of the inhibitory protein, IκB-α, and the NF-κB-DNA binding activity. The essential oil from the leaves of *J. oxycedrus* in a concentration of 0.02% (v/v) achieved the greatest inhibition (80±8%) of IL-1-induced NO production. Chemical analysis showed that this essential oil is predominantly composed of monoterpene hydrocabons, being α-pinene [2,6,6-trimethyl-bicyclo(3.1.1)hept-3-ene] the major constituent (76%). Similarly to the effect of the whole oil, a fraction containing 93% α-pinene reduced significantly IL-1-induced IκB-α degradation. Moreover, α-pinene also decreased IκB-α phosphorylation, NF-κB-DNA binding activity, and NO production. Another fraction containing oxygenated mono- and sesquiterpenes was nearly as effective as α-pinene. The ability of the α-pinene-containing fraction to reduce IL-1-induced NF-κB activation and NO production warrants further studies to demonstrate the usefulness of α-pinene in the treatment of arthritic diseases and other conditions in which NF-κB and NO play pathological roles." So alpha pinene also decreases Nitric Oxide production. It is capable of crossing the blood brain barrier. According to Miyazawa et al.: "Inhibition of acetylcholinesterase (AChE) activity by 17 kinds of bicyclic monoterpenoids was investigated. Bicyclic monoterpenoids are contained in many kinds of essential oils. Inhibition of AChE was measured according to the colorimetric method. 3.1.1 and 4.1.0 bicyclic hydrocarbons with allylic methyl group showed strong inhibition. (+)- and (−)-alpha-pinene and (+)-3-carene were potent inhibitors of AChE. 3.1.1 and 2.2.1 bicyclic alcohols and ketones showed weak inhibition. 3.1.1 and 4.1.0 bicyclic hydrocarbons with allylic methyl group were found to be uncompetitive inhibitors."

Thus, "in vitro" inhibition has been proven and "in vivo" effectiveness can be inferred from Martinez et al.: "*Salvia lavandulifolia* Vahl. is a plant from the Iberian peninsula whose phytochemical evaluation indicated the presence of flavonoids, triterpenoids, diterpenoids and monoterpenes. It has an essential oil rich in various bioactive compounds (like 1,8-cineole or α-pinene). It has been traditionally used for its spasmolytic, antiseptic, analgesic, sedative and anesthesic activities. Pharmacological studies of the plant have demonstrated its reputation as aromatic plant to enhance memory and anti-dementia drug by the inhibition of cholinesterase enzyme. The species also possesses a wide range of pharmacological uses including: antioxidant, anti-inflammatory, estrogenic and central nervous system depressant properties, relevant to the treatment of Alzheimer's disease. The present review summarizes the information concerning the taxonomy ecological and biogeographical features, ethnopharmacology, phytochemistry, pharmacological activities and toxicity of the *Salvia lavandulifolia* because these findings suggest the need for further research on this species."

Finally, and making reference also to camphene, let us quote Chien-Tsong et al.: "In this study, the fruit essential oil of *Cinnamomum insularimontanum* was prepared by using water distillation. Followed by GC-MS analysis, the composition of fruit essential oil was characterized. The main constituents of essential oil were α-pinene (9.45%), camphene (1.70%), β-pinene (4.30%), limonene (1.76%), citronellal (24.64%), citronellol (16.78%), and citral (35.89%). According to the results obtained from nitric oxide (NO) inhibitory activity assay, crude essential oil and its dominant compound (citral) presented the significant NO production inhibitory activity, IC50 of crude essential oil and citral were 18.68 and 13.18 μg/mL, respectively. Moreover, based on the results obtained from the protein expression assay, the expression of IKK, iNOS, and nuclear NF-κB was decreased and IκBα was increased in dose-dependent manners, it proved that the anti-inflammatory mechanism of citral was blocked via the NF-κB pathway, but it could not efficiently suppress the activity on COX-2. In addition, citral exhibited a potent anti-inflammatory activity in the assay of croton oil-induced mice ear edema, when the dosage was 0.1 and 0.3 mg per ear, the inflammation would reduce to 22% and 83%, respectively. The results presented that the fruit essential oil of *C. insularimontanum* and/or citral may have a great potential to develop the anti-inflammatory medicine in the future."

To conclude this section, a robust anti-inflammatory action that can cross the blood brain barrier from many compounds in high concentration from rosemary essential oil can be inferred.

However, oral ingestion of essential oils is strongly discouraged. From Millet Y. et al.: " . . . The occurrence of intoxications induced by essential oils of sage and hyssop from commercial origins brings into question the nature of toxic constituents . . . " and " . . . clinical observations involved experimental work to demonstrate the Central Nervous System (CNS) toxicity and to analyze the chemical composition of two commercial oils, oil of sage and oil of hyssop." Quoting the University of New Hampshire Health Services: "Is aromatherapy safe? If done correctly, aromatherapy is a very safe practice. However, because some plants contain harmful toxins, it is important to understand the oil and how to apply it. Never put undiluted oils directly on the skin (except lavender and tea tree oil for certain skin conditions), and keep them away from the eyes and from open flames. Oils should also never be swallowed."

According to Cook et al.: "Aromatherapy is the use of concentrated essential oils extracted from herbs, flowers, and other plant parts to treat various diseases." Plant oils are distilled without the use of chemicals by heating the plant through boiling or steaming until the oil vaporizes. The oil is then used in a variety of different ways, such as for massage, as a steam inhalation, as bath oil or as vaporizers for a living space. We will use any commercial vaporizer to dilute the essential oil, resulting vapors in the air of a living space and will follow a modified protocol taken from Zahra N et al.'s protocol: " . . . inhalation aromatherapy with lavender aroma twice a day (10-11 AM and 6-7 PM) subsequent days (second and third days of hospitalization); these times were selected based on the schedule of treatment and care in related units and the time of patients rest. Each session of aromatherapy lasted for twenty minutes . . . "

The claimed subject matter uses any commercial vaporizer where 3 to 5 drops of commercial rosemary essential oil will be sprinkled on the apposite pad, and will vaporize on demand (nicotine craving episode) for 10 min. with a maximum frequency of 5 times/day.

Referring now to FIG. 2, nicotinamide, also known as niacinamide and nicotinic amide, is the amide of nicotinic acid (vitamin B3/niacin). Nicotinamide is a water-soluble vitamin and is part of the vitamin B group. Nicotinic acid, also known as niacin, is converted to nicotinamide in vivo, and, though the two are identical in their vitamin functions, nicotinamide does not have the same pharmacological and toxic effects of niacin, which occur incidental to niacin's conversion. FIG. 2 is a perspective view of the molecular structure 200 of niacinamide. In the present embodiment, the chemical formula of niacinamide is C6H6N2O and the molecular weight is 122.1. In the present embodiment, the toxicity of LD50 for a mouse is 2500 mg/Kg, for a rat is 3500 mg/Kg.

Niacinamide is also a iNOS inhibitor as demonstrated by LeClaire et al., whose work's abstract is quoted below: "The effect of staphylococcal enterotoxin B (SEB)-elicited inducible nitric oxide synthase (iNOS) in mouse endothelial cells was investigated. Results showed that SEB stimulated the same level of NO production in gamma interferon (IFN)-primed cells as did trichloroacetic acid-extracted lipopolysaccharide. The kinetics of induced NO production and expression of mRNA for iNOS differed markedly in endothelial and macrophage cells. Induced endothelial nitrite production was transient and was 15 to 20% of that generated by macrophage cells; mRNA levels peaked by 2 h and then steadily declined, whereas macrophage message levels continually increased. The ability of endothelial cells to produce SEB-induced NO depended on priming with IFN, although detectable mRNA could be elicited by SEB alone. Induction of endothelial iNOS mRNA was inhibited by cycloheximide, which indicated a requirement for de novo protein synthesis. Niacinamide and interleukin-10 significantly reduced SEB-induced endothelial NO production. Both are reported to affect IFN-gamma-induced class II major histocompatibility complex (MHC) expression on antigen-presenting cells. Niacinamide reduced iNOS mRNA levels and markedly reduced IFN-gamma induction of endothelial class II MHC surface antigen. Interleukin-10 did not consistently reduce iNOS mRNA expression and had no effect on IFN-induction of endothelial class II MHC surface antigen. These results suggest that SEB interacts with IFN-gamma-primed endothelial cells to elicit induced NO and that this induction can be effectively modulated at the receptor or transcriptional level."

In Chia-Chih et al., one may read "Abstract Background: Phorbol myristate acetate (PMA) is a strong neutrophil activator and has been used to induce acute lung injury (ALI). Niacinamide (NAC) is a compound of B complex. It exerts protective effects on the ALI caused by various challenges. The purpose was to evaluate the protective effects of niacinamide (NAC) on the PMA-induced ALI and associated changes.

Methods: The rat's lungs were isolated in situ and perfused with constant flow. A total of 60 isolated lungs were randomized into 6 groups to received Vehicle (DMSO 100 μg/g), PMA 4 μg/g (lung weight), co-treated with NAC 0, 100, 200 and 400 mg/g (lung weight). There were 10 isolated lungs in each group. We measured the lung weight and parameters related to ALI. The pulmonary arterial pressure and capillary filtration coefficient (Kfc) were determined in isolated lungs. ATP (adenotriphosphate) and PARP [poly(adenosine diphophate-ribose) polymerase] contents in lung tissues were detected. Real-time PCR was employed to display the expression of inducible and endothelial NO synthases (iNOS and eNOS). The neutrophil-derived mediators in lung perfusate were determined.

Results: PMA caused increases in lung weight parameters. This agent produced pulmonary hypertension and increased microvascular permeability. It resulted in decrease in ATP and increase in PARP. The expression of iNOS and eNOS was upregulated following PMA. PMA increased the neutrophil-derived mediators. Pathological examination revealed lung edema and hemorrhage with inflammatory cell infiltration. Immunohistochemical stain disclosed the presence of iNOS-positive cells in macrophages and endothelial cells. These pathophysiological and biochemical changes were diminished by NAC treatment. The NAC effects were dose-dependent.

CONCLUSIONS

Our results suggest that neutrophil activation and release of neutrophil-derived mediators by PMA cause ALI and associated changes. NO production through the iNOS-producing cells plays a detrimental role in the PMA-induced lung injury. ATP is beneficial, while PARP plays a deteriorative effect on the PMA-induced ALI. NAC exerts protective effects on the inflammatory cascade leading to pulmonary injury. This B complex compound may be applied for clinical usage and therapeutic regimen." Thus, the anti-inflammatory capacity of niacinamide are clear, where the inducible nitric oxide synthase expression is effectively inhibited in rat's tissue.

In human beings, it has also proven its anti-inflammatory value. Quoting Adeghate et al. work's abstract: "Neural cells are found in all organs of the body and play an important role in the maintenance of the internal milieu. The pancreatic beta cell is the most numerous cell types in the endocrine pancreas. It is particularly important because of its role in insulin secretion, a crucial hormone in glucose metabolism. In view of this, the significance of the survival of neural and pancreatic beta cell cannot be over emphasized. Neural and pancreatic beta cell death occurs in a variety of ways. The destruction of neural cells can be induced with (1) free radicals (H2O2, O2-, HO—) and nitric oxide; (2) Cytokines (tumor necrosis factor, interleukin-1 beta, interferon-gamma); (3) Glutamate; (4) Amphetamine analog (Ecstasy); (5) S100 protein; (6) Ammonia; (7) Iron ions; (8) Resins, e.g. methylmethycrylate. Pancreatic beta cell can be destroyed by (1) free radicals (H2O2, O2-, HO—) and nitric oxide; (2) Cytokines (tumor necrosis factor, interleukin-1 beta, interferon-gamma); (3) alkylating agents (streptozotocin, alloxan, N-methyl-nitrosourea N-ethyl-N-nitrosourea, Methylmethanesulphonate and ethylmethanesulphonate); (4) hyperglycaemia; (5) islet amyloid polypeptide; and (6) Inositol Monophosphate dehydrogenase inhibitors. There is enough evidence that most of these agents involved in neural and pancreatic beta cell death exert their toxic effects through the nitric oxide pathway. Neuroprotective agents include vitamin B12 analogs and alpha-tocopherol, NOS inhibitors, antioxidants (e.g. glutathione, superoxide dismutase), metals like cobalt, neurotrophic receptors (Akt kinase) and growth factors. The pancreatic beta cell death induced by these toxic agents can be prevented and or delayed by nicotinamide (vitamin B3), heat shock, copper, alpha-tocopherol (vitamin E), succinic acid, dihydroxylipoic acid, fusidic acid, glucocorticoids, cyclosporin A, growth factors and gene therapy."

As to niacinamide's ability to cross the Blood Brain Barrier (BBB), it is a given as stated by Spector et al.: "With the application of genetic and molecular biology techniques, there has been substantial progress in understanding how vitamins are transferred across the mammalian blood-brain bather and choroid plexus into brain and CSF and how vitamin homeostasis in brain is achieved. In most cases (with the exception of the sodium-dependent multivitamin transporter for biotin, pantothenic acid, and lipoic acid), the vitamins are transported by separate carriers through the blood-brain barrier or choroid plexus. Then the vitamins are accumulated by brain cells by separate, specialized systems. This review focuses on six vitamins (B1, B3, B6, pantothenic acid, biotin, and E) and the newer genetic information including relevant 'knockdown' or 'knockout' models in mice and humans. The overall objective is to integrate this newer information with previous physiological and biochemical observations to achieve a better understanding of vitamin transport and homeostasis in brain. This is especially important in view of the newly described non-cofactor vitamin roles in brain (e.g. of B1, B3, B6, and E) and the potential roles of vitamins in the therapy of brain disorders. Keywords: cerebral endothelium, choroidal epithelium, CSF homeostasis, ependyma, niacinamide, pyridoxine, thiamine, vitamer transporters, a-tocopherol." In conclusion, niacinamide can cross the blood brain barrier.

Figure 3:
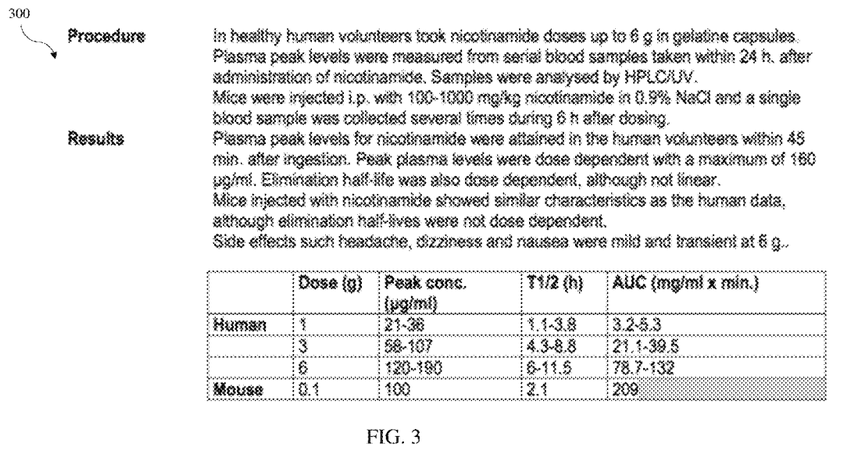
FIG. 3 is a section of a study illustrating the pharmacodynamics of niacinamide, according to an example embodiment.

Regarding the pharmacodynamics of niacinamide, quoting the Stratford et al. study: "The pharmacokinetics of nicotinamide were studied in four human volunteers after oral doses of 1-6 g. Plasma concentrations and clearance rates of the vitamin were found to be dose-dependent, with a half-life of ~7-9 h for the two highest doses administered (4 and 6 g), ~4 h with 2 g and ~1.5 h with a 1-g dose. Peak concentrations ranged from 0.7 to 1.1 µmol·ml-1 after a 6-g dose. The time to reach peak plasma concentration was dose independent with a broad range from 0.73 to 3 h. In this study, nicotinamide had no detectable effect on blood pressure, pulse or body temperature." Another source is the excellent IPCS (International Programme on OECD SIDS 3-PYRIDINECARBOXAMIDE (NICOTINAMIDE)). FIG. 3 illustrates a section of a study 300 illustrating the pharmacodynamics of niacinamide. Both studies agree on increasing half-lives when dosages are increased. Also there's fair agreement in cautiously assuming a half-life of 4 hours for humans.

Regarding experimental safe levels of niacinamide, quoting the excellent SIDS Initial Assessment Report for SIAM 15, 3-Pyridinecarboxamide (nicotinamide), p. 15: "In studies with diabetic and at-risk-of-diabetes patients who were treated for several years with 1.5 to 3 g nicotiniamide daily (25 and 42 mg/kg/day, respectively) no effect on a range of biochemical parameters including liver and kidney function tests was observed (ref. 120, 121)." Using only half of lowest experimented dosage, i.e. 12.5 mg/Kg, then an 85 Kg person would ingest slightly over 1.0 g a day. Available commercial dosages are 500 mg. This, 500 mg of niacinamide every 3×T1/2=12 hours, being T1/2=4 hours, would result in a very cautious and safe dose. In short: 500 mg every 12 to 24 hours is preferable. Without entering into unnecessary complications dealing with body surface area or body mass index, lighter individuals can safely use a half dosage compared to heavier peers: 250 mg every 12 to 24 hours.

Regarding resolution of suspected under-regulated D-serine expression as a neuroadaptation from chronic exposure to nicotine, since D-serine is very probably downregulated, there must be means to either supplement it or to slow its metabolism or recapture. Quoting Supplison et al.: "In the central nervous system of Vertebrates, diffusion and uptake of neurotransmitters by specific transporters terminate synaptic transmission at the notable exception of acetylcholine which is hydrolyzed by acetylcholinesterase. Transporters of recapture are located in glial cells and/or neurons and uptake regulates the basal extracellular concentration and spillover of neurotransmitters, thus limiting synaptic cross talk. Though recapture is their principal mode of operation, transporters are bi-directional molecular machines and may also behave as a Ca+2-independent source of neurotransmitters, depending on the direction of the driving force." One of the transporters belongs to a Na+/Cl-coupled co-transporters family and is called the glycine transporters 1 and 2 (GlyT-2).

Continuing with Supplison's work "Glycine is a neuromodulator of excitatory transmission as a high affinity co-agonist with glutamate of NMDA receptors . . . . Since no evidence for a mechanism of co-liberation of glycine and glutamate has been reported, it is assumed that the occupancy of the glycine co-agonist site relies on the resting extracellular glycine GlyB and D-serine concentrations. At present, specific D-serine transporters have not been reported and it is not clear how D-serine which is synthesized in astrocytes is exported out of the cell, then degraded or recaptured from the extracellular space. Nevertheless, an action of D-serine or glycine requires in the first place that transporters are able to lower GlyB to submicromolar levels in the synaptic cleft."

Quoting now Yang et al.: "Endogenous glycine and d-serine both act as co-agonists on the strychnine-insensitive GlyB site on the NMDA receptor, and along with glutamate, co-activate the NMDA receptor. Forebrain synaptic glycine and d-serine levels are regulated by the Glycine Transporter-1 (GlyT1) and the arginine-serine-cysteine transporter-1 (Asc-1), respectively; in addition to d-serine metabolism by d-Amino Acid Oxidase (DAAO). Together, these processes prevent the GlyB site from being saturated by the high extracellular levels of brain glycine, and perhaps d-serine, in vivo. Blockade of NMDA receptors by phencyclidine induces schizophrenia-like symptoms with the associated cognitive deficits. It was proposed that: a) blockade of GlyT1 mediated reuptake of glycine, or b) inhibition of d-amino Acid Oxidase, or Asc-1 will elevate brain glycine, and d-serine to upregulate NMDA receptor functions via glycine and d-serine co-agonistic allosteric modulation of the GlyB sites on the NMDA receptor."

As it turns out, Asc-1 has high affinity for both glycine and D-serine, as stated in Xie et al.'s work: "The Na+-independent alanine-serine-cysteine transporter 1 (Asc-1) is exclusively expressed in neuronal structures throughout the central nervous system (CNS). Asc-1 transports small neutral amino acids with high affinity especially for d-serine and glycine (Ki: 8-12 µM), two endogenous glutamate co-agonists that activate N-methyl-d-aspartate (NMDA) receptors through interacting with the strychnine-insensitive glycine binding-site. By regulating d-serine (and possibly glycine) levels in the synaptic cleft, Asc-1 may play an important role in controlling neuronal excitability,"

Thus both Asc-1 and GlyT will transport D-serine and that inhibition of function to anyone of both transporters will necessarily increase the concentration of D-serine in the synaptic cleft and its consequent NMDA r-function increase.

Quoting Javitt et al's work: "A second-generation approach to NMDAR stimulation has been the use of glycine transport (GlyT1) inhibitors. GlyT1 transporters are colocalized in the CNS with NMDAR and serve to maintain low, sub-saturating glycine concentrations within the protected space of the synaptic cleft. Initial behavioral studies were performed with the glycine derivative glycyldodecylamide (GDA) and physiological studies with NFPS (ALX-5407) Subsequent studies have shown the effectiveness of high-affinity glycine transport inhibitors in a range of preclinical models relevant to schizophrenia, including PCP-induced hyperactivity and dopaminergic dysregulation. Significant clinical results have been obtained with sarcosine (N-methylglycine), a naturally occurring glycine transport inhibitor, and, most recently, with the high-affinity glycine transport inhibitor R1678."

Sarcosine is commercially available, has a proven scientific track record when used in schizophrenia patients, and currently has no known toxicity. Quoting Amiaz et al.: "This current study has evaluated the safety, tolerability and pharmacokinetics of 2 and 4 gm/d of sarcosine in order to test the possible use of this compound as add-on treatment for schizophrenia. In general, sarcosine was well tolerated by the patients. Administration of sarcosine at 2 and 4 gm/d for one week appears to be safe. No significant events, abnormal laboratory results or ECG abnormalities related to the study medication were noted. As previously mentioned, early termination of this study was due to one article presenting some evidence that sarcosine can cause exacerbation of prostate cancer (10). However, later studies failed to replicate these findings and one other study has been published showing the opposite (11, 30). Furthermore, there is another ongoing NIH funded study that examines the effects of sarcosine on brain glycine concentrations (ClinicalTrials.gov identifier: NCT00538070). To the best of our knowledge, this is the first study that presents pharmacokinetic evaluations of sarcosine. The pharmacokinetic results show that sarcosine concentration in serum reaches its peak after two hours, and the half-life of sarcosine is approximately one hour. These results indicate that sarcosine should be administered at least twice a day. It light of the above, it can be concluded that sarcosine is a safe compound, without significant side effects and with a relatively short half-life."

Figure 4:
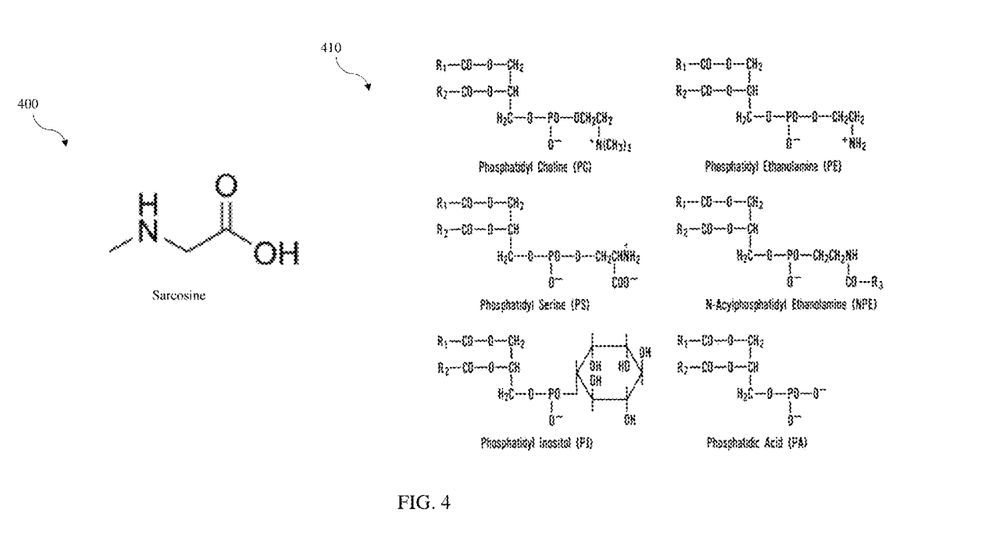
FIG. 4 is a perspective view of the molecular structure of sarcosine, according to an example embodiment.

Since the half-life is 1 hour, then it should be administered every 3 hours to keep a constant presence of drug both in plasma and then of course in synaptic cleft where its action is needed. Regarding dosage, experimental works find a mere 300 mg oral dosage for an individual of 190 pounds to be efficacious. Lighter/smaller individuals may safely use a 200 mg dosage. Total daily dosage does not exceed 300 mg/time×5 times/day=1500 mg/day which is sensibly lower than what has been used in research with schizophrenia patients in most studies, with no side effects observed whatsoever. FIG. 4 is a perspective view of the molecular structure 400 of sarcosine. The chemical formula of sarcosine is C3H7NO2 and has a molar mass of 89.09 g·mol-1.

Regarding resolution of reduced GABAergic function as a consequence of chronic nicotine use and under expressed DAr2 through homeostatic compensation mechanisms, in as much as the GABAergic inputs to Dopamine neurons in the nucleous accumbens work as a counterbalancing mechanism, a "brake" to the excitatory dopaminergic neurotransmission in its tonic expression, it is coding for "wanting" brain reward, rather than "liking" it. Thus it is preferable to counterbalance the excitatory state either by increasing GABAergic function or decreasing the dopaminergic function. A simple, safe and readily available way is to downregulate the production of dopamine neurotransmitters interfering with its synthesis. Quoting Yangha Kim et al.: "Catecholamines are among the first molecules that displayed a kind of response to prolonged or repeated stress. It is well established that long-term stress leads to the induction of catecholamine biosynthesis enzymes such as tyrosine hydroxylase (TH) and Dopamine beta-hydroxylase (DBH) in adrenal medulla. The aim of the present study was to evaluate the effects of *ginseng* on TH and DBH mRNA expression. Repeated (2 h daily, 14 days) immobilization stress resulted in a significant increase of TH and DBH mRNA levels in rat adrenal medulla. However, *ginseng* treatment reversed the stress-induced increase of TH and DBH mRNA expression in the immobilization-stressed rats. Nicotine as a ligand of the nicotinic acetylcholine receptor (nAChR) in adrenal medulla stimulates catecholamine secretion and activates TH and DBH gene expression. Nicotine treatment increased mRNA levels of TH and DBH by 3.3- and 3.1-fold in PC12 cells. The *ginseng* total saponin exhibited a significant reversal in the nicotine-induced increase of TH and DBH mRNA expression, decreasing the mRNA levels of TH and DBH by 57.2% and 48.9%, respectively in PC12 cells. In conclusion, immobilization stress induced catecholamine biosynthetic enzymes gene expression, while *ginseng* appeared to restore homeostasis via suppression of TH and DBH gene expression. In part, the regulatory activity in the TH and DBH gene expression of *ginseng* may account for 67th anti-stress action produced by *ginseng*." For rigorous estimation of a Human Equivalent Dose (HED), one may use Reagan-Shaw et al.'s work. Using Reagan-Shaw et al.'s work: HED=200 mg/kg×(6/37)=32.43 mg/Kg or an 80 Kg individual, Dosage: ~2500 mg/day.

Figure 5:
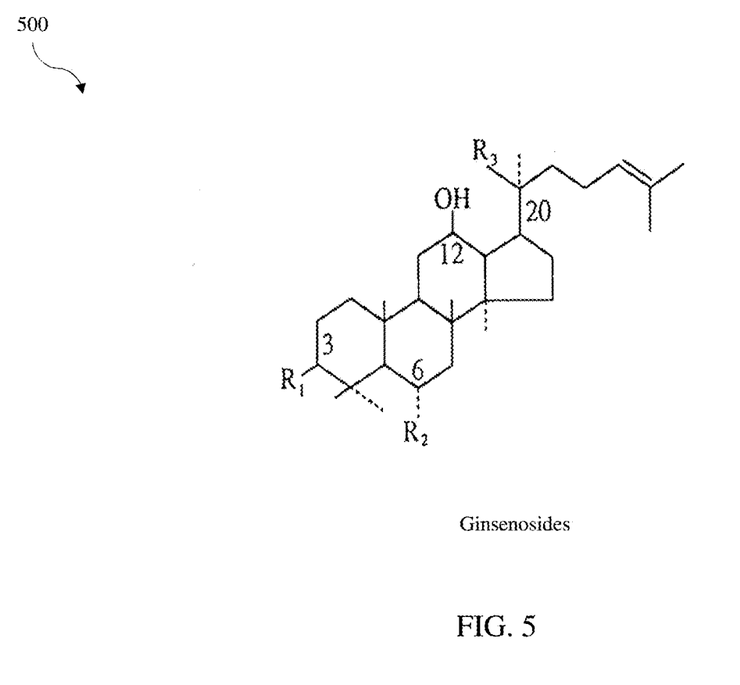
FIG. 5 is a perspective view of the molecular structure of a general diagram of the five representative ginsenosides, according to an example embodiment.

As an experimental dose, half a dosage may safely be used, that is, 600 mg every 12 hours, for a daily total of 1200 mg based on the safety record of I-Ju et al.'s work, where 3500 mg daily were used and no significant side effects were observed. For subjects lighter in weight, 45 to 55 Kg, half dose may be used, so 600 mg a day, in two doses of 300 mg every 12 hours. The latter study duration was 2 months while the instant protocol should not last more than 5 to 7 days. A standardized extract of 15% ginsenosides is preferably used. From Seok Choi et al.'s work, FIG. 5 is a perspective view of the molecular structure 500 of a general diagram of five representative ginsenosides.

Regarding resolution of under expressed DAr2 through homeostatic compensation mechanisms, dopamine DA receptors DA1, DA2 become under expressed as a consequence of chronic nicotine use. Quoting Wanderoy et al.'s work: "1. Human dopamine (DA) D2long (hD2L) receptors, expressed by Ltk-cells, can be up-regulated by treating the cells with forskolin for 16 hr (Johansson and Westlind-Danielsson, 1994). We have examined some of the molecular mechanisms underlying this forskolin-mediated up-regulation. 2. forskolin (100 µM, 16 hr), but not 1,9-dideoxyforskolin, a forskolin analogue that is unable to activate adenylyl cyclase and raise intracellular cAMP concentrations, up-regulates the hD2L receptor population by 43%. The implication of a cAMP-dependent increase in the receptor up-regulation was further substantiated by treating the cells with 8-bromo-cAMP or prostaglandin E1 (PGE1). The forskolin-mediated rise in receptor number was blocked by cycloheximide or an antisense phosphorothioate oligodeoxynucleotide (ODN) directed toward the hD2L mRNA. KT5720, a specific protein kinase A (PKA) inhibitor, completely blocked the receptor rise, whereas pertussis toxin (PTX) attenuated the increase considerably. Forskolin also produced an increase in the level of the DA hD2short (hD2S) receptor expressed by Ltk-cells. This increase was 2.5-fold higher than that found for the hD2L receptor. 3. The forskolin-mediated hD2L receptor rise is dependent on de novo protein synthesis, a rise in cAMP levels, PKA activation, and, at least partially, PTX-sensitive G proteins."

Long-term increases in intracellular cAMP levels may change the sensitivity of a DA receptor expressing cell to DA by increasing D2 receptor density through enhanced cAMP-dependent transcription. Since forskolin will increase DA2 receptor expression in cell cultures, and no study in humans has evaluated this possibility to this date. Using Godard et al's study: 250 mg of 10% forskolin extract twice a day can be used with no significant side effects observed.

Figure 6:
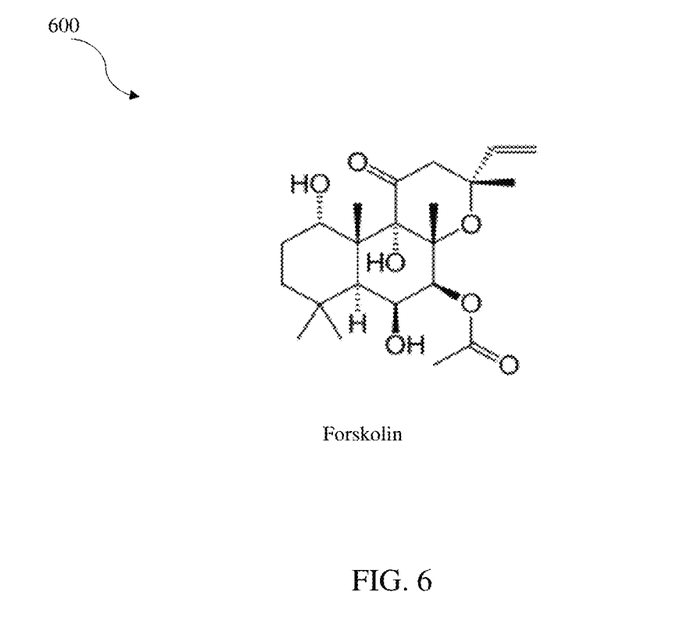
FIG. 6 is a perspective view of the molecular structure of forskolin, according to an example embodiment.

The following is toxicity data of forskolin: oral LD50 (rat): 2,550 mg/kg; oral LD50 (mouse): 3,100 mg/kg; using the rat's data and Reagan-Shaw's work; and HED=2550× (6/37)=413 mg/Kg, in a 100 pound (45.4 Kg) person, LD50 may be estimated at 413 mg×45.4 Kg=18,773.51 mg. Hence 500 mg/day of forskolin 10% extract may be estimated as totally safe, with no toxicity whatsoever expected, except for possible allergic reactions. FIG. 6 is a perspective view of the molecular structure 600 of forskolin, according to an example embodiment. The chemical formula of forskolin is C22H3407 and the molar mass is 410.50116.

Regarding the resolution of transient hypoglycemic state during nicotine withdrawal, as explained above, when taking into account that acetylcholine, which is in downregulation mode in tobacco smokers in early abstinence, is also a paracrine signal priming human beta cell function, then faulty regulation of glucose concentration in plasma derives in the hypoglycemic condition. Quoting Rodriguez-Diaz et al.: "Acetylcholine is crucial for pancreatic beta cell function. Acetylcholine stimulates insulin secretion by increasing the cytoplasmic free Ca+2 concentration, [Ca+2]I, via inositol phosphate production and enhancing the effects of Ca+2 on exocytosis via protein kinase C in beta cells. Muscarinic receptors found in pancreatic beta cells are essential for maintaining proper insulin secretion and glucose homeostasis in mice. Cholinergic agonists have been reported to restore defective glucose-stimulated insulin secretion."

The proper cholinergic agonist is abundant in some foods like eggs, soybeans, mustard, sunflower and it is called phosphatidylcholine. Regarding phosphatidylcholine's toxicity, Kidd P.'s work reads: "In the trials cited in this review, PC was very well tolerated at oral intakes that ranged up to 4.6 grams per day, and was found to be more effective the earlier it was administered." Commercially, there are many soy lecithin concentrate preparations that naturally include phosphatidyl choline, which recommended daily dose is: "The recommended adequate intake (AI) for choline has been set at 425 mg/d for women, 450 mg/d for pregnant women, 550 mg/d for lactating women and 550 mg/d for men." Any commercially available preparation will include the aforementioned dosage in 1 capsule a day of soy lecithin. FIG. 4 shows a perspective view of the molecular structure 410 of various phosphatides in soy lecithin.

Figure 7:
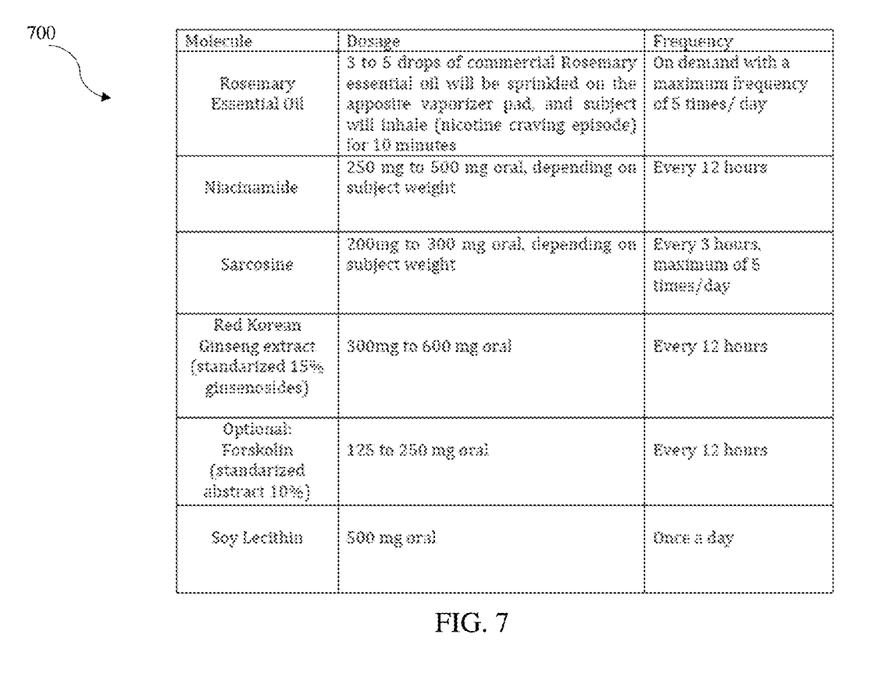
FIG. 7 is a table of a treatment protocol for alleviating cravings and discomfort upon immediate cessation of tobacco use sustained by nicotine addition, according to an example embodiment; and, FIG. 8 is a drawing depicting a view of the claimed subject matter depicting its use.

Finally and in summary, regarding a treatment protocol for alleviating cravings and discomfort upon immediate cessation of tobacco use sustained by nicotine addiction, the protocol 700 illustrated in FIG. 7 is to be used upon immediate nicotine cessation, and will be used for 5 to 7 days, or until nicotine cravings subside, whichever happens first. In any case, it must not be prolonged more than 14 days.

Figure 8:
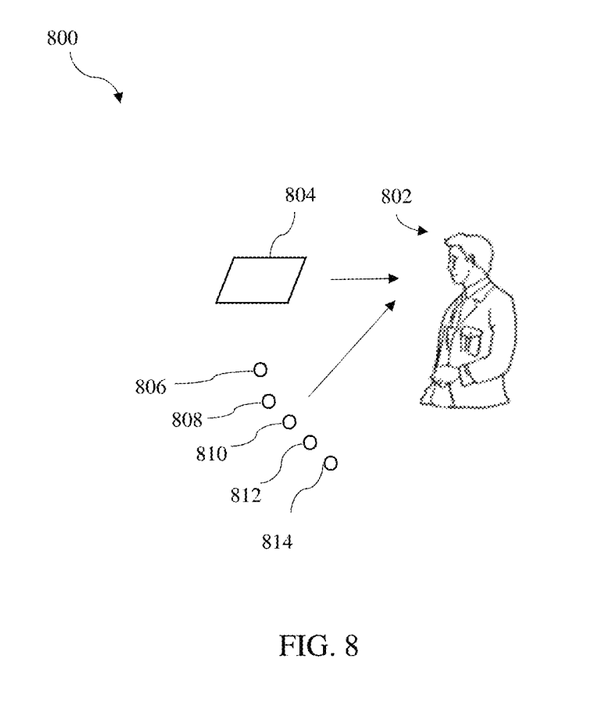

FIG. 8 is a view of the claimed subject matter depicting its use as protocol 800. User 802 may also follow protocol 700 as illustrated in FIG. 7. As mentioned above, the protocol may be used upon immediate nicotine cessation, and will be used for 5 to 7 days, or until nicotine cravings subside, whichever happens first. In any case, such protocol must not be prolonged for more than 14 days. The protocol includes a user 802 inhaling, upon commencement of a nicotine craving episode, for about 10 minutes, about between 3 to 5 drops of rosemary essential oil. The rosemary essential oil may be sprinkled on an apposite vaporizer pad 804. The maximum frequency that user 802 should inhale the rosemary essential oil sprinkled on an apposite vaporizer pad is about five times per day. The protocol includes a user orally ingesting, about every 12 hours, an amount of niacinamide 806, wherein each amount of niacinamide is about between 250 mg to 500 mg and such amount or dosage may be varied depending on a user's weight. The protocol includes a user orally ingesting, about every 3 hours, an amount of sarcosine 808, wherein each amount of sarcosine is about between 200 mg to 300 mg and such amount may be varied depending on a user's weight. The maximum number of dosages of sarcosine 808 a user should intake is about 5 times daily. The protocol includes a user orally ingesting, about every 12 hours, an amount of red Korean *ginseng* extract 810, wherein each amount of red Korean *ginseng* extract 810 is about between 300 mg to 600 mg. The protocol includes a user orally ingesting, about once a day, an amount of soy lecithin 814, wherein each amount of soy lecithin is about 500 mg. Optionally, the protocol further includes the user orally ingesting, about every 12 hours, an amount of forskolin 812, wherein each amount of forskolin is about between 125 mg to 250 mg. As mentioned above the protocol is to be used upon immediate nicotine cessation, and will be used for 5 to 7 days, or until nicotine cravings subside, whichever happens first. In any case, it must never be prolonged more than 14 days.

*Ginseng* is the name given to at least three different plants. The most widely used *ginseng* is *Panax ginseng*, variously known as Asian, Chinese, or Korean *ginseng*. American *ginseng*, *Panax quinquefolius*, is also considered a true *ginseng*. Even though all three ginsengs are used as tonics, herbalists and others familiar with herbal remedies tend to use them for different purposes. Korean *ginseng* is considered to be the most potent or stimulating type of *ginseng*.

Recent scientific studies have shed some light on the different natures of the two true ginsengs. Korean *ginseng* has been shown to contain more Rg1 ginsenosides, which have more stimulating effects, whereas American *ginseng* has a higher percentage of Rb1 ginsenosides, which have more sedating effects. *Panax ginseng* has long been considered to be one of the great healing and strengthening herbs in natural medicine. *Ginseng* is classified as an adaptogen, which is a substance that helps the body adapt to stress and balance itself without causing major side effects. Korean *ginseng* is used as a tonic for improving overall health and stamina, and Chinese herbalists particularly recommend it for the ill, weak, or elderly. Korean *ginseng* has long been asserted to have longevity, anti-senility, and memory improvement effects in the aged population. As it helps the body to adapt to stress, athletes may use *ginseng* as herbal support during rigorous training. Korean *ginseng* generally increases physical and mental energy. It is a good tonic for the adrenal glands, and is used by those suffering from exhaustion, burnout, or debilitation from chronic illness.

Traditional Chinese medicine also prescribes Korean *ginseng* to treat diabetes, and research has shown that it enhances the release of insulin from the pancreas and lowers blood sugar levels. Korean *ginseng* has been demonstrated to lower blood cholesterol levels. It has also been shown to have antioxidant effects and to increase immune system activity, which makes it a good herbal support for those suffering from cancer and AIDS and other chronic conditions that impair the immune system. Further uses of Korean *ginseng* in Chinese medicine include treatment of impotence, asthma, and digestive weakness.

Scientists have isolated what they believe are the primary active ingredients in *ginseng*, chemicals termed saponin triterpenoid glycosides, or commonly called ginsenocides. There are nearly 30 ginsenocides in Korean *ginseng*. Recent research in China was summarized by Dr. C. Lui in the February 1992 issue of the Journal of Ethnopharmacology, where he wrote that *Panax ginseng* was found to contain 28 ginsenocides that "act on the central nervous system, cardiovascular system and endocrine secretion, promote immune function, and have effects on anti-aging and relieving stress." Korean *ginseng* has been shown in studies to have significant effects for physical improvement and performance enhancement for athletes, Mental performance improvement and mood enhancement, anti-fatigue and anti-stress actions, lowering blood sugar, antioxidant properties, cholesterol reduction, anticancer effects and immune system stimulation, physical and mental improvement in the elderly, and impotence.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A method for alleviating cravings and discomfort of a nicotine user due to nicotine addiction upon immediate cessation of tobacco by said nicotine user, comprising:
   a) the nicotine user inhaling, upon commencement of a nicotine craving episode, for about 10 minutes, between about 3 to 5 drops of rosemary essential oil, wherein said rosemary essential oil is sprinkled on an apposite vaporizer pad, and wherein said inhaling step is performed a maximum of 5 times daily;
   b) the nicotine user orally ingesting, about every 12 hours, between about 250 mg to 500 mg of niacinamide;
   c) the nicotine user orally ingesting, about every 3 hours, between about 200 mg to 300 mg of sarcosine;
   d) the nicotine user orally ingesting, about every 12 hours, between about 300 mg to 600 mg of red Korean *ginseng* extract;
   e) the nicotine user orally ingesting, about once a day, about 500 mg of soy lecithin; and,
   f) the nicotine user orally ingesting, about every 12 hours, between about 125 mg to 250 mg of forskolin;

wherein said method is performed until said cravings and discomfort subside in said nicotine user and for a maximum of approximately 14 days.

\* \* \* \* \*